United States Patent [19]

Barnish et al.

[11] 4,299,820
[45] Nov. 10, 1981

[54] THERAPEUTIC PROCESS EMPLOYING AMIDES OF L AND DL PHENYLGLYCINES

[75] Inventors: Ian T. Barnish, Ramsgate; Peter E. Cross; John C. Danilewicz, both of Canterbury, all of England

[73] Assignee: Pfizer Inc., New York, N.Y.

[21] Appl. No.: 126,104

[22] Filed: Feb. 29, 1980

Related U.S. Application Data

[63] Continuation of Ser. No. 900,802, Apr. 27, 1978, abandoned.

[30] Foreign Application Priority Data

May 6, 1977 [GB] United Kingdom ............... 19001/77

[51] Int. Cl.$^3$ ....................... A61K 37/00; A61K 31/24
[52] U.S. Cl. .................................... 424/177; 424/309; 260/112.5 R
[58] Field of Search ................. 260/112.5 R; 424/177, 424/309

[56] References Cited

U.S. PATENT DOCUMENTS

| | | | |
|---|---|---|---|
| 2,948,714 | 8/1960 | Amiard et al. ............... | 260/112.5 R |
| 3,891,696 | 6/1975 | Bodor et al. ........................ | 560/40 |
| 4,017,636 | 4/1977 | Jones et al. ......................... | 424/309 |
| 4,064,235 | 12/1977 | Yanaihara et al. ................... | 424/177 |
| 4,087,520 | 5/1978 | Braun et al. ................. | 260/112.5 R |
| 4,128,474 | 12/1978 | Barnish et al. ....................... | 424/319 |
| 4,148,920 | 4/1979 | Barnish et al. ...................... | 424/319 |
| 4,179,520 | 12/1979 | Barnish et al. ....................... | 424/309 |
| 4,179,521 | 12/1979 | Barnish et al. ....................... | 424/309 |
| 4,185,116 | 1/1980 | Barnish et al. ....................... | 424/319 |
| 4,185,117 | 1/1980 | Barnish et al. ....................... | 424/324 |
| 4,186,210 | 1/1980 | Barnish et al. ....................... | 424/324 |
| 4,243,672 | 1/1981 | Barnish et al. ....................... | 424/274 |

OTHER PUBLICATIONS

Jobin et al., "Thrombosis et Diathesis Haemorrhagica", (Stuttgart), 22 (3), 468-481, 1969.
Chem. Absts., 54, 4408, (1960).
Greenstein et al., "Chemistry of the Amino Acids", John Wiley and Sons, Inc., New York, 19, vol. I, pp. vii-x.
Higgins et al., Life Sciences 27, 963-970, (1980).

Primary Examiner—Frank Cacciapaglia, Jr.
Attorney, Agent, or Firm—Connolly and Hutz

[57] ABSTRACT

Derivates of L- and DL-hydroxyphenylglycines of the formula

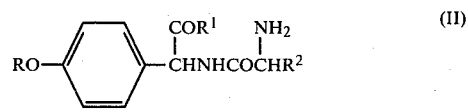

and the pharmaceutically acceptable salts thereof, wherein R is hydrogen or methyl, $R^1$ is hydrogen, amino or alkoxy having from one to six carbon atoms and $R^2$ is the residue of certain α-amino acids are useful in treating diseases and conditions which are characterized by reduced blood flow, oxygen availability or carbohydrate metabolism in the cardiovascular system. Derivatives of D-hydroxyphenylglycine of formula (II) are substantially inactive in treating such diseases and conditions.

13 Claims, No Drawings

THERAPEUTIC PROCESS EMPLOYING AMIDES OF L AND DL PHENYLGLYCINES

CROSS REFERENCE TO RELATED APPLICATION

This application is a continuation of application Ser. No. 900,802, filed Apr. 27, 1978, now abandoned.

BACKGROUND OF THE INVENTION

1. Field of the Invention

The invention relates to novel derivatives of L- and DL-hydroxyphenylglycine of formula (II) as defined herein and pharmaceutically acceptable salts thereof, their use in treating diseases and conditions of mammalian subjects including humans, which are characterized by reduced blood flow, reduced oxygen availability or reduced carbohydrate metabolism in the cardiovascular system; and pharmaceutical compositions thereof.

2. Description of the Prior Art

In co-pending United States application Ser. No. 834,768 filed Sept. 19, 1977, now U.S. Pat. No. 4,148,920 known L- and DL-phenylglycines of the formula

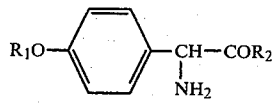
(I)

where $R_1$ is hydrogen or methyl and $R_2$ is $NH_2$, OH or completes a carboxylic ester group, are disclosed as being useful in treating diseases and conditions characterized by reduced blood flow, oxygen availability or carbohydrate metabolism in the cardiovascular system. Such conditions include ischaemic heart disease (particularly angina pectoris and myocardial infarction), cardiac failure and cerebral insufficiency. The compounds are also useful in other diseases involving defects in carbohydrate metabolism such as obesity and diabetes.

Dipeptide derivatives of L-tyrosine with common amino acids, but not hydroxyphenylglycine, are well known in the art. Their preparation is described in Chemical Abstracts, 54, 4408 (1960). However, no biological activity is disclosed for such peptides.

N-Aminoacyl derivatives of L-DOPA (3,4-dihydroxy-L-phenylalanine) which are useful in the treatment of Parkinson's disease are also known. They are disclosed, for example, in U.S. Pat. No. 3,891,696. In particular, this patent discloses 3,4-dihydroxy-L-phenylalanyl-L-isoleucine and its methyl ester as transient pro-drug forms of L-DOPA.

SUMMARY OF THE INVENTION

The present invention provides novel derivatives of L- and DL-p-hydroxyphenylglycine having unexpected advantages comprising a p-hydroxyphenylglycine fragment and an aminoacyl fragment, said derivatives being of the formula

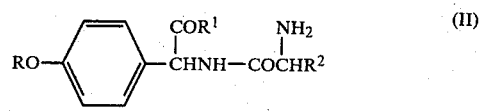
(II)

where R is hydrogen or methyl; $R^1$ is hydroxy, amino or alkoxy having from one to six carbon atoms; $R^2$ is a member selected from the group consisting of hydrogen, phenyl, hydroxyphenyl, benzyl, p-hydroxybenzyl, alkyl having from one to six carbon atoms and $-(CH_2)_n COOR^5$, where n is 1 or 2 and $R^5$ is hydrogen, methyl or ethyl; and the pharmaceutically acceptable salts thereof.

By the term "p-hydroxyphenylglycine fragment" is meant that portion of the compound of formula (II) that is derived from p-hydroxyphenylglycine, said fragment is of the formula

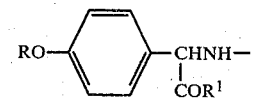

wherein R and $R^1$ are as defined above.

By the term "aminoacyl fragment" is meant the remaining portion of the compound of formula (II), said fragment is of the formula

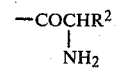

wherein $R^2$ is as previously defined.

While the p-hydroxyphenylglycine fragment of the compounds of formula (II) may be racemic (DL), it is preferably of the L-configuration. The aminoacyl fragment may be present as the L, D, or DL form; however, it is preferably present in the L-configuration, particularly when derived from a naturally-occurring amino acid.

Especially preferred compounds and salts of formula (II) are those wherein R is hydrogen, $R^1$ is an hydroxy group or methoxy group and those wherein $R^2$ is 4-hydroxyphenyl, methyl or sec-butyl.

Particularly preferred compounds of formula (II) are:
L,L-N-alanyl-2-(4-hydroxyphenyl)glycine,
L,L-methyl N-alanyl-2-(4-hydroxyphenyl)glycinate,
L,L-N-isoleucyl-2-(4-hydroxyphenyl)glycine,
L,L-methyl-N-isoleucyl-2-(4-hydroxyphenyl)glycinate,
L,L-N-[2-(4-hydroxyphenyl)glycyl]-2-(4-hydroxyphenyl)glycine and
L,L-methyl-N-[2-(4-hydroxyphenyl)glycyl]-2-(4-hydroxyphenyl)glycinate.

The invention further provides a method of treating mammalian subjects, including humans, suffering from a disease or condition attributable to reduced blood flow, oxygen availability or carbohydrate metabolism which comprises orally or parenterally administering to said subject a blood flow, oxygen availability or carbohydrate metabolism increasing amount of a compound of formula (II) or a pharmaceutically acceptable salt thereof.

Also provided are pharmaceutical compositions comprising a pharmaceutically acceptable carrier and a blood flow, oxygen availability or carbohydrate metabolism increasing amount of a compound of formula (II) or a pharmaceutically acceptable salt thereof.

DETAILED DESCRIPTION OF THE INVENTION

According to the present invention, novel derivatives of L- and DL-p-hydroxyphenylglycine are provided of the formula

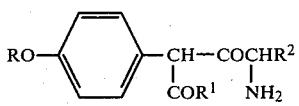

and the pharmaceutically acceptable salts thereof, wherein R, $R^1$ and $R^2$ are as previously defined.

Pharmaceutically acceptable salts of compounds of the formula (II) include addition salts with acids containing pharmaceutically acceptable anions, e.g. the hydrochloride, hydrobromide, sulphate or bisulphate, phosphate or acid phosphate, acetate, maleate, fumarate, succinate, lactate, tartrate, citrate, gluconate, saccharate and p-toluene sulphonate salts. When $R^1$ is OH or $R^5$ is hydrogen, pharmaceutically acceptable salts also include salts with pharmaceutically acceptable cations, e.g. the sodium, potassium, calcium and ammonium salts.

The L-form is the preferred form of the compounds of formula (I), the D-form being substantially inactive. It will therefore be appreciated that compounds of formula (II) derived from L-phenylglycine derivatives will be substantially more active than those derived from the racemic (DL) form.

The novel compounds of formula (II) may be prepared using the classic protecting and coupling techniques of amino-acid chemistry for example as described in "Chemistry of the Amino Acids" by J. P. Greenstein and M. Winitz. Thus the carboxyl group in 4-hydroxy-phenylglycine is protected by esterification and the product is coupled to an N-protected aminoacid derivative using a coupling reagent or activated ester technique. The N-blocking group is removed to yield the esters of formula (II), preferred esters are those in which $R^1$ is alkoxy having from one to six carbon atoms, or both blocking groups are removed to yield the acids of formula (II) wherein $R^1$ is a hydroxyl group.

The general method employed to prepare the valuable compounds of formula (II) is illustrated by the following reaction scheme.

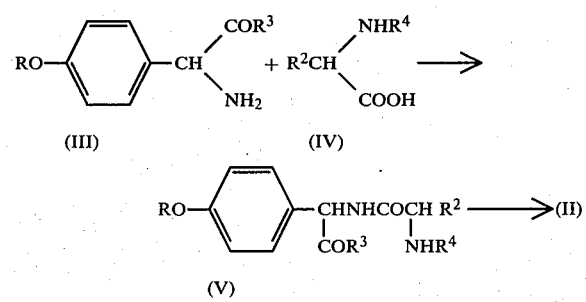

Starting material (III) is an amino ester or amide in which R is as previously defined and $R^3$ is $NH_2$ or alkoxy having from one to six carbon atoms. In reactant (IV) $R^2$ is as previously defined and $R^4$ is an amino protecting group. In carrying out the above process the acid of formula (IV) is first converted to a reactive derivative capable of acylating the amino compound (III). While $R^4$ may be any of the amino protecting groups known in the art for use in peptide synthesis (see, e.g., "Peptides", Edited by Zervas, Pergamon Press, New York, 1966, pp. 3–118.), a particularly preferred value for amino protecting group $R^4$ is t-butyloxycarbonyl. This group is readily introduced by reaction of the appropriate amino acid with t-butyloxycarbonyl azide by the procedure of Grzonka et al., Synthesis, 661 (1974), and is easily removed from the intermediate of formula (V) by treatment with acid.

Reaction of the amine of formula (III) with a reactive derivative of an acid of the formula (IV) may be achieved in various ways; for example, via a mixed anhydride prepared from the acid of formula (IV) by reaction with a chloroformate e.g. ethyl chloroformate, or by preparing an activated ester of said acid, e.g., with N-hydroxysuccinimide and dicyclohexylcarbodiimide, N-t-Butyloxycarbonyl amino acid N-hydroxysuccinimide esters are known compounds and their preparation is described for example by Anderson et al., in J. Amer. Chem. Soc., 86, 1839 (1964). For example, the reaction with 2-(4-hydroxyphenyl)glycine methyl ester is conveniently performed with the reactants dissolved in a reaction-inert organic solvent, e.g., 1,2-dimethoxyethane or tetrahydrofuran, and is generally complete within 24 hours at room temperature. The product is isolated by conventional techniques, e.g., by evaporation of the solvent under vacuum and the product is purified, if necessary, by solvent extraction and recrystallization. The N-blocking t-butyloxycarbonyl group is removed by acid treatment, e.g., by treatment with a solution of hydrogen bromide in glacial acetic acid at room temperature or with gentle warming for several minutes, and the ester product is generally isolated by precipitation with ether and further purified by solvent extraction or recrystallization. Alternatively, the ester group is first hydrolyzed by treatment with an aqueous solution of sodium hydroxide in a conventional manner and the N-blocking group is then removed as before to yield the acid product of formula (II) wherein $R^1$ is a hydroxyl group.

As mentioned above, the phenylglycine derivatives of formula (I) are known compounds. Methods for the preparation of the DL-compounds and their subsequent resolution into the D- and L-forms are well known (see, for example, U.S. Pat. No. 3,976,680).

The compounds of the formula (II) may be administered to patients in admixture with or dissolved in a pharmaceutically acceptable carrier selected with regard to the intended route of administration and standard pharmaceutical practice. For example, they may be administered orally in the form of tablets or capsules containing a unit dose of the compound of the formula (II) together with such excipients as corn starch, calcium carbonate, dicalcium phosphate, alginic acid, lactose, magnesium stearate, talc, or certain complex silicates. The tablets are typically prepared by granulating the ingredients together and compressing the resulting mixture to tablets of the desired size. The capsules are typically prepared by granulating the ingredients together and filling them into hard gelatin capsules of the appropriate size to contain the ingredients.

The compounds of the invention may also be administered parenterally, for example by intramuscular, intravenous or subcutaneous injection. For parenteral administration, they are best used in the form of a sterile aqueous solution which may contain other solutes, for example enough salts (e.g. sodium acetate, sodium lactate, sodium succinate or sodium chloride) or dextrose to make the solution isotonic. A pharmaceutically-acceptable organic solvent such as polyethylene glycol or ethanol may also replace part of the water. An antioxidant such as sodium metabisulphite may also be present, typically in an amount up to 0.1% by weight. Such parenteral formulations may be prepared by conventional methods. For example, in a typical procedure involving the preparation of a succinate-containing intravenous formulation, a 0.2 molar solution of succinic acid may be mixed with a 0.2 molar solution of sodium hydroxide to give a solution of pH 5. The compound of the formula (II) is then typically dissolved in the succinate solution in an amount of 1–2% on a weight/volume basis. The resulting solution may then be sterilized, for example by filtration, through a bacteria-proof filter under aseptic conditions into sterile containers.

Alternatively, stable parenteral formulations based on isotonic saline solution may be prepared by successively dissolving an antioxidant, e.g. sodium metabisulphite, and sodium chloride in nitrogen-sparged water to give an approximately 0.1 molar sodium chloride solution, dissolving the compound of formula (II) in solution in an amount of 1–2% on a weight/volume basis and adjusting the pH to about 4 with 0.1 N hydrochloric acid. The solution is then sterilized and filled into containers as already described. Suitable containers are, for example, sterile glass vials of an appropriate size to contain the desired volume of solution, which volume will typically contain one or more unit doses of the compound of the formula (II). The compounds of the formula (II) may also be administered by the infusion of a parenteral formulation as described above into a vein.

For oral or parenteral administration to human patients the dosage level of a compound of formula (II) wherein the p-hydroxyphenylglycine fragment is of the L-configuration is from about 0.5 to 20 mg./kg. and especially 2 to 10 mg./kg. for a typical adult patient (50–70 kg.), said dose being administered up to 5 times a day. Thus, a typical unit dose would contain from about 25 to 1400 mg. of the active compound. Tablets or capsules will preferably contain from about 100 mg. to 700 mg. of the active compound, one or more of which would be taken orally up to 5 times a day. Dosage units for parenteral administration will preferably contain from 100–700 mg. of the active compound in 30–50 ml. of solution. A typical vial could thus be a 50 ml. vial containing from 2 to 25 mg. of the active compound per ml. in 30–50 ml. of solution. The dosage level of the DL-(racemic) form of the compounds will, of course, be about twice that of the L-form.

It should, of course, be appreciated that the physician in any event will determine the actual dosage which will be most suitable for the individual and it will vary with the age, weight and response of the patient. The above dosages are exemplary of the average host. There may, of course, be individual cases where higher or lower dosage ranges are merited.

The utility of the compounds of the formula (II) for treating disease or conditions characterized by reduced blood flow, oxygen availability or carbohydrate metabolism in the cardiovascular system, or other disease or condition involving a defect in carbohydrate metabolism, particularly diabetes and obesity, is assessed by their ability:

(1) to increase the oxidation of glucose and/or pyruvate by isolated rat muscle preparations in vitro;
(2) to increase the proportion of the active form of the enzyme pyruvate dehydrogenase (PDH) in organs of animals in vivo;
(3) to reduce oxygen demand and affect the relative utilization of carbohydrate and lipid metabolites by the electrically-paced heart of anesthetized dogs in the presence or absence of an isoprenaline stimulus; and
(4) to decrease the blood glucose levels in animals made diabetic by chemical lesion of the pancreas.

Activity in tests for (1) illustrates the utility of the compounds in the treatment of ischaemic heart disease, cardiac failure, cerebral insufficiency, maturity-onset diabetes or obesity. Activity in tests for (2) further illustrates their utility in the treatment of these diseases or conditions and, in particular, activity in an animal heart in vivo demonstrates utility in the treatment of ischaemic heart disease and cardiac failure, while activity in animal brain in vivo is a measure of utility in the treatment of cerebral insufficiency. Activity in tests for (3) further illustrates their utility in the treatment of ischaemic heart disease and cardiac failure. Activity in tests for (4) is a further measure of their utility in the treatment of diabetes.

Representative compounds of the formula (II) have been tested for their ability to increase the oxidation of glucose and/or pyruvate as follows:

Diaphragm tissue is obtained from rats fed on a high fat diet similar to 'Diet B' described by Zaragoza and Felber [Horm.Metab. Res., 2, 323 (1970)]. Pyruvate oxidation by such tissue is assessed by measurement of the rate of incorporation of carbon-14 from carbon-14-labelled pyruvate into carbon dioxide in vitro, as described by Bringolf [Eur. J. Biochem., 26, 360 (1972)]. The rate of pyruvate oxidation is depressed by 50%–75% compared with that by diaphragm tissue from rats fed on a normal diet. When the compounds of the formula (II) are added to the medium, they are found to stimulate pyruvate oxidation by diaphragm tissue from fat-fed rats in a dose dependent manner.

The degree of stimulation obtained with several of the compounds of formula (II) is shown in the following table:

| Compound of Example: | Concentration, mM | % Stimulation |
|---|---|---|
| 1 | 0.25 | 23 |
| 3 | 0.25 | 39 |
| 7 | 2 | 61 |
| 8 | 2 | 23 |
| 9 | 2 | 35 |
| 10 | 2 | 10 |

The ability of compounds of formula (II) to increase the proportion of the active form of the pyruvate dehydrogenase enzyme has been measured in the following test:

Rats fed on a high fat diet as in the previous test, are treated either with placebo or with the compound of formula (II) by subcutaneous or intravenous injection or by oral administration. After 1½ hours the rat hearts are removed and homogenized under conditions which minimize changes in the proportion of the pyruvate dehydrogenase enzyme (PDHt) which is present in the active form, as described by Whitehouse and Randle [Biochem. J., 134, 651 (1973)]. The total amount of the enzyme present (PDHt) and the amount which is present in the active form (PDHa) are assessed by a method similar to that described by Taylor et al. [J. Biol. Chem., 248, 73 (1973)]. The fat-feeding process is found to depress the ratio PDHa/PDHt from a normal value of about 0.7 to a value in the range from 0.05 to 0.2. Treatment of fat-fed rats with the compounds of formula (II) either parenterally or orally, increases this ratio in a dose-dependent manner.

The increase in the PDHa/PDHt ratio effected by the compounds of formula (II) at the dose level indicated is shown in the following table:

| Example No. | Dose (mmoles/kg.) | PDHa/PDHt ratio | |
|---|---|---|---|
| | | placebo | compound |
| 1 | 1.2 p.o | 0.13 | 1.00 |
| 3 | 1.2 p.o. | 0.13 | 0.75 |
| 8 | 0.6 p.o. | 0.09 | 0.56 |
| | 0.6 s.c. | 0.09 | 0.77 |
| 9 | 1.2 p.o. | 0.09 | 0.24 |
| | 1.2 s.c. | 0.09 | 0.48 |
| 10 | 0.6 p.o. | 0.09 | 0.72 |
| | 0.6 s.c. | 0.09 | 0.86 | s.c. = subcutaneous
p.o. = oral

The preparation of the novel compounds of the invention is illustrated by the following examples.

EXAMPLE 1

A. L-N-tert-Butyloxycarbonyl-2-(4-hydroxyphenyl)glycine

This was obtained from L(+)-2-(4-hydroxyphenyl)glycine and t-butyloxycarbonylazide by the method of Grzonka and Lammek [Synthesis, 661 (1974)]. Crystallization from hexane-ethyl acetate afforded material suitable for further synthesis in yields typically 68–90%; M.P. 114°–115° C. (decomp.); $[\alpha]_D^{28} = +128°$ (1.02%, methanol). Recrystallization from aqueous ethanol afforded pure material of M.P.=115°–117° C. (decomp.), $[\alpha]_D^{28} = +135°$ (1.01%, methanol).

B. L-Methyl-2-(4-hydroxyphenyl)glycinate

Thionyl chloride (8.95 ml., 0.123 mole) was added dropwise to stirred methanol (120 ml.) at −5° to −10° C., then L(+)-2-(4-hydroxyphenyl)glycine (18.72 g., 0.112 mole) was added in portions. The resulting solution was stirred at room temperature for one hour and then under reflux for one hour. The methanol was removed under vacuum to provide a syrup which, upon trituration with ether, afforded the hydrochloride salt as a white solid. The dry salt was dissolved in water (400 ml.) and the resulting solution was cooled and treated with concentrated aqueous ammonia until a pH of 9 was obtained. The white precipitate was collected by filtration and successively triturated with 2-propanol (twice) then ether (twice) and dried under vacuum to yield the ester (17.0 g., 84%), M.P. 188°–190° C. (decomp.); $[\alpha]_D^{26} = +141.4°$ (1%, 1 N HCl).

Found: C, 59.81; H, 6.07; N, 7.47%. Calculated for $C_9H_{11}NO_3$: C, 59.66; H, 6.12; N, 7.73%

C. L,L-Methyl N-[N-tert-butyloxycarbonyl-2-(4-hydroxyphenyl)glycyl]-2-(4-hydroxyphenyl)glycinate hemihydrate The product from Part A, above (5.3 g., 0.02 mole) was dissolved in dry tetrahydrofuran (50 ml.) and the stirred solution was cooled to −5° C. and treated with triethylamine (2.1 g., 0.021 mole). Ethyl chloroformate (2.2 g., 0.020 mole) was added dropwise to the resulting suspension and stirring was continued at −5° to 0° C. for 10 minutes before the portion-wise addition of a slurry of the product from Part B (3.6 g., 0.02 mole) in dry tetrahydrofuran (25 ml.) over 10 minutes. The reaction mixture was stirred at 0° C. for 0.5 hours, then at room temperature for two hours, before evaporation of the solvent under vacuum. The residue was partitioned between ethyl acetate (100 ml.) and water (100 ml.), the ethyl acetate extract separated and successively washed with water (50 ml.), 2 N hydrochloric acid (50 ml.), water (50 ml.), 5% aqueous sodium bicarbonate solution (50 ml.) and water (50 ml.). Evaporation of the dried (MgSO$_4$) ethyl acetate solution gave an oil which, on trituration with ether, furnished the solid product (6.2 g., 72%), M.P. 165°–167° C. (decomp.) with softening at ca. 130° C., $[\alpha]_D^{26} = +115.3°$ (1.03%, methanol).

Found: C, 59.89; H, 5.90; N, 6.24%; Calculated for $C_{22}H_{26}N_2O_7 \cdot \frac{1}{2}H_2O$: C, 60.12; H, 6.19; N, 6.38%

D. L,L-Methyl N-[2-(4-hydroxyphenyl)glycyl]-2-(4-hydroxyphenyl)glycinate hydrobromide The product from Part C (2.0 g., 0.00465 mole) was added, in portions, to a stirred, ice-cold, 45% solution of hydrogen bromide in glacial acetic acid (7 ml.). The resulting frothing suspension was stirred for five minutes at room temperature, then warmed gently until dissolution was complete. After being stirred at room temperature for a further 20 minutes, the solution was added, with stirring, to dry ether (150 ml.) to provide a gum. Trituration of the gum with ether, followed by digestion of the crude product with boiling ethyl acetate, filtration and drying under vacuum, gave the product (1.32 g., 71%), M.P. 212°–215° C. (decomp.); $[\alpha]_D^{27} = +84.5°$ (1.02%, methanol).

Found: C, 49.08; H, 4.71; N, 6.63%; Calculated for $C_{17}H_{18}N_2O_5 \cdot HBr$: C, 49.65; H, 4.66; N, 6.81%

EXAMPLE 2

By repeating the procedure of Part B of Example 1 but employing the appropriate alcohol in place of the methanol used therein and either L(+)-2-(4-hydroxyphenyl)glycine or L(+)-2-(4-methoxyphenyl)glycine, the following L-amino esters are similarly obtained.

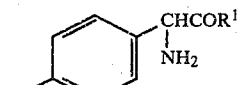

| R | R$^1$ |
|---|---|
| CH$_3$ | OCH$_3$ |
| H | OCH$_2$CH$_3$ |
| CH$_3$ | OCH$_2$CH$_3$ |
| H | OCH(CH$_3$)$_2$ |
| CH$_3$ | O(CH$_2$)$_3$CH$_3$ |
| H | O(CH$_2$)$_5$CH$_3$ |
| CH$_3$ | O(CH$_2$)$_3$CH(CH$_3$)$_2$ |

Employing DL-2-(4-hydroxyphenyl)glycine or DL-2-(4-methoxyphenyl)glycine in the above procedure provides the corresponding racemic amino esters.

EXAMPLE 3

A. L,L-N-[N-tert-butyloxycarbonyl-2-(4-hydroxyphenyl)glycyl]-2-(4-hydroxyphenyl)glycine A solution of sodium hydroxide (1.5 g., 0.0375 mole) in water (37.5 ml.) was added to a stirred solution of the product from Example 1, Part C (3.3 g., 0.00755 mole) in a mixture of 1,4-dioxan (100 ml.) and water (25 ml.). After 0.5 hours hydrolysis was complete (by thin-layer chromatography) and the reaction solution was diluted with water (25 ml.) and its pH adjusted to 7 using 2 M aqueous citric acid solution. The 1,4-dioxan was removed by evaporation under vacuum and then the pH of the residual aqueous solution was adjusted to ca 3 with 2 M aqueous citric acid solution. Extraction with ethyl acetate (2×100 ml.), washing with water and drying (MgSO$_4$) of the combined ethyl acetate extracts, followed by evaporation under vacuum yielded a foam, which was triturated with hexane and dried under vacuum to give a powder.

Further trituration with ethyl acetate followed by filtration, washing with hexane and drying, afforded the acid (2.5 g., 80%) as a white solid, M.P. 198°–201° C. (decomp.); $[\alpha]_D^{27} = +135.5°$ (0.95%, MeOH).

Found: C, 60.09; H, 5.65; N, 6.94%; Calculated for C$_{21}$H$_{24}$N$_2$O$_7$: C, 60.57; H, 5.81; N, 6.73%.

B. L,L-N-[2-(4-hydroxyphenyl)glycyl]-2-(4-hydroxyphenyl)glycine hydrobromide hemihydrate The product from Part A, above (1.5 g., 0.0036 mole) was added, in portions, to a stirred, ice-cold, 45% solution of hydrogen bromide in glacial acetic acid (5 ml.). The resulting frothing suspension was stirred for five minutes at room temperature, then warmed gently until dissolution was complete. Upon stirring at room temperature for 20 minutes, the solution afforded a precipitate. The mixture was poured into stirred, dry ether (100 ml.), and the resulting solid was collected, digested with ethyl acetate (50 ml.) and dried under vacuum furnishing the product (1.38 g., 96%), M.P. 253°–256° C. (decomp.); $[\alpha]_D^{26} = +98.0°$ (1% methanol).

Found: C, 47.02; H, 4.30; N, 6.46%; Calculated for C$_{16}$H$_{16}$N$_2$O$_5$·HBr·1/2H$_2$O: C, 47.30; H, 4.47; N, 6.90%.

EXAMPLE 4

Employing the amino esters provided in Example 2 as starting material in place of L-methyl-2-(4-hydroxyphenyl)glycinate in the procedure of Example 1, Part C, and hydrolysis of t-butyloxycarbonyl group of the resulting product by the procedure of Part D of Example 1, the following L- or DL- amino esters are obtained as the hydrobromide salts.

RO—⟨C$_6$H$_4$⟩—CH(COR$^1$)NHCOCH(NH$_2$)—⟨C$_6$H$_4$⟩—OH

| R    | R$^1$             |
|------|-------------------|
| CH$_3$ | OCH$_3$           |
| H    | OCH$_2$CH$_3$     |
| CH$_3$ | OCH$_2$CH$_3$     |
| H    | OCH(CH$_3$)$_2$   |
| CH$_3$ | O(CH$_2$)$_3$CH$_3$ |
| H    | O(CH$_2$)$_5$CH$_3$ |
| CH$_3$ | O(CH$_2$)$_3$CH(CH$_3$)$_2$ |

The corresponding free bases of the above structure are obtained by neutralisation with aqueous ammonia, extraction with chloroform and evaporation of the extracts to dryness.

EXAMPLE 5

L,L-N-[2-(4-Hydroxyphenyl)glycyl]-2-(4-hydroxyphenyl)glycine amide

L,L-Methyl N-[2-(4-hydroxyphenyl)glycyl]-2-(4-hydroxyphenyl)glycinate hydrobromide from the procedure of Example 1, Part D, 10 g., is dissolved in a small amount of water, rendered basic with dilute ammonium hydroxide solution and the free base extracted with benzene, extracts washed with sodium bicarbonate solution, water, then dried over MgSO$_4$ and evaporated to dryness in vacuo. The residue is dissolved in 250 ml. of dry methanol and dry ammonia gas is passed through the mixture for two hours. The resulting mixture is allowed to stand overnight at 0° C., filtered and the filtrate evaporated in vacuo to obtain the title amide.

Employing the amino ester hydrobromides provided in Example 4 in the above procedure, the corresponding compounds wherein R$^1$ is NH$_2$ are obtained in each case.

EXAMPLE 6

By employing the appropriate t-butyloxycarbonyl amino acid in place of L-N-t-butyloxycarbonyl-2-(4-hydroxyphenyl)glycine in the coupling procedure of Example 1, Part C and hydrolysis of the resulting N-t-butoxycarbonyl dipeptide ester with hydrobromic and acetic acids by the procedure of Example 1, Part D, the following dipeptide esters of L-2-(4-hydroxyphenyl)glycine are obtained in each case as the hydrobromide salts.

HO—⟨C$_6$H$_4$⟩—CH(COOCH$_3$)—NHCOCH(NH$_2$)—R$^2$

| t-Butyloxycarbonyl (t-Boc) Amino Acid | R$^2$ |
|---------------------------------------|-------|
| t-Boc—L-phenylalanine                 | C$_6$H$_5$CH$_2$ |
| t-Boc—glycine                         | H |
| t-Boc—DL-phenylglycin                 | C$_6$H$_5$ |
| t-Boc—L-tyrosine                      | 4-HOC$_6$H$_4$CH$_2$ |
| t-Boc—DL-α-aminocaprylic acid         | CH$_3$(CH$_2$)$_5$ |

When DL-ethyl 2-(4-hydroxyphenyl)glycinate is employed in place of L-methyl 2-(4-hydroxyphenyl)glycinate in the above procedure the corresponding dipeptide ethyl esters of DL-2-(4-hydroxyphenyl)glycine are similarly obtained.

The t-butyloxycarbonyl amino acids are either obtained from commercial sources or by the method described by Grzonka, Synthesis, 661 (1974).

EXAMPLE 7

A. L,L-Methyl N-(N-tert-butyloxycarbonylalanyl)-2-(4-hydroxyphenyl)-glycinate

A suspension of L-methyl 2-(4-hydroxyphenyl)glycinate (5.45 g., 0.03 mole) in dry 1,2-dimethoxyethane (60 ml.) was added to a stirred suspension of L-N-t-butyloxycarbonylalanine N-hydroxysuccinimide ester (8.6 g., 0.03 mole) obtained by the method of Anderson et al., J. Am. Chem. Soc., 86, 1839 (1964), in dry 1,2-dimethoxyethane (60 ml.) under nitrogen at room temperature. The reaction mixture gradually became clearer to afford a thin, milky suspension, which was stirred for 70 hours. The mixture was diluted with water (400 ml.) then concentrated under vacuum and extracted with ethyl acetate (200 then 100 ml.). The combined ethyl acetate extracts were washed with water (2×100 ml.), dried (MgSO$_4$) and evaporated under vacuum to provide an oil. Treatment with boiling hexane (2×100 ml.), followed by prolonged standing under hexane, produced a gum which hardened in the absence of solvent. Crushing and drying in vacuo gave a cream powder (9.5 g., 90%), M.P. from ca. 67° C. (decomp.); $[\alpha]_D^{27} = +92.4'$ (1%, methanol).

Found: C, 58.08; H, 7.06; N, 7.40%; Calculated for C$_{17}$H$_{24}$N$_2$O$_6$: C, 57.94; H, 6.87; N, 7.95%.

B. L,L-Methyl N-alanyl-2-(4-hydroxyphenyl)glycinate hydrobromide

The product from Part A, above (2.45 g., 0.007 mole), was added in portions to a stirred, ice-cold 45% solution of hydrogen bromide in glacial acetic acid (10 ml.). The resulting frothing suspension was stirred at room temperature for 15 minutes, then briefly warmed (5 minutes) until dissolution was complete. After being stirred at room temperature for a further 20 minutes, the solution was added, with stirring, to dry ether (150 ml.) to give a brownish-orange gum. The ether was decanted and the gum allowed to stand under more dry ether overnight. The resulting toffee was crushed, digested with ether then with hot ethyl acetate, and dried under vacuum, to furnish the product as a pinkish-cream powder (1.9 g., 82%), M.P. from ca. 122° C. (decomp.); $[\alpha]_D^{24} = +120.3°$ (1%, methanol).

Found: C, 43.16; H, 5.14; N, 8.38%; Calculated for $C_{12}H_{16}N_2O_4 \cdot HBr$: C, 43.25; H, 5.14; N, 8.41%.

EXAMPLE 8

A. L,L-N-(N-tert-butyloxycarbonylalanyl)-2-(4-hydroxyphenyl)glycine

A solution of sodium hydroxide (3.0 g., 0.075 mole) in water (75 ml.) was added to a stirred solution of the product from Example 7, Part A (5.28 g., 0.015 mole) in a mixture of 1,4-dioxan (200 ml.) and water (40 ml.). After 0.5 hours, the pH of the reaction solution was adjusted to 7 using 2 M aqueous citric acid solution and the 1,4-dioxan removed by evaporation under vacuum. The pH of the residual solution was adjusted to 3.5 with 2 M aqueous citric acid solution and the solution was extracted with ethyl acetate (2×100 ml.). The combined extracts were washed with water (2×100 ml.), dried (MgSO$_4$), and evaporated under vacuum to afford a foaming oil. Successive triturations with n-hexane, followed by grinding and drying under vacuum, gave the acid as a creamish powder (4.5 g., 89%), M.P. from ca. 85° C. (decomp.); $[\alpha]_D^{26.5} = +76.1°$ (1%, methanol).

Found: C, 55.13; H, 6.71; N, 7.12%; Calculated for $C_{16}H_{22}N_2O_6$: C, 56.79; H, 6.55; N, 8.28%.

B. L,L-N-Alanyl-2-(4-hydroxyphenyl)glycine hydrobromide

The product from Part A, above (3.0 g., 0.008 mole), was treated with a 45% solution of hydrogen bromide in glacial acetic acid (10 ml.) as described in Example 7, Part B. The resulting gum was twice triturated with ether and then with hot ethyl acetate to yield a hygroscopic gum which, on further treatment with ether and ethyl acetate at room temperature, followed by rapid drying under vacuum, grinding, and further drying under vacuum provided the product (1.93 g., 58%) as a pinkish-gray powder, M.P. from ca 120° C. (decomp.); $[\alpha]_D^{26} = +113.2°$ (1%, methanol).

Found: C, 43.42; H, 5.41; N, 7.07%; Calculated for $C_{11}H_{14}N_2O_4 \cdot HBr \cdot 2/3 CH_3CO_2Et$: C, 43.43; H, 5.42; N, 7.41%

EXAMPLE 9

A. L,L-Methyl N-(N-tert-butyloxycarbonylisoleucyl)-2-(4-hydroxyphenyl)-glycinate A suspension of L-methyl 2-(4-hydroxyphenyl)glycinate (10.85 g., 0.06 mole) in dry 1,2-dimethoxyethane (120 ml.) was added to a stirred solution of crude L-N-tert-butyloxycarbonyl-isoleucine N-hydroxy succinimide ester (20.5 g.) in dry 1,2-dimethoxyethane (60 ml.) under nitrogen at room temperature. The resulting suspension was stirred for 74 hours and thinned considerably. The orange mixture was filtered to remove a small quantity of solid, then diluted with water (400 ml.). The oil which precipitated solidified on stirring and then standing at room temperature, and the dark pink product was collected, washed with water and dried under vacuum at 100° C. Crystallization from petroleum ether (b.p. 60°–80° C.)/ethyl acetate provided the product (13.2 g., 56%) as a pale pink solid, M.P. 145.5°–146.5° C.; $[\alpha]_D^{24} = +84.3°$ (1%, methanol).

Found: C, 60.79; H, 7.60; N, 7.22%; Calculated for $C_{20}H_{30}N_2O_6$: C, 60.89, H, 7.67; N, 7.10%.

B. L,L-Methyl N-isoleucyl-2-(4-hydroxyphenyl)-glycinate hydrobromide monohydrate The product from Part A, above (3.95 g., 0.01 mole), was treated with a 45% solution of hydrogen bromide in glacial acetic acid (15 ml.) as described in Example 7, Part B. Successive trituration and decantation with dry ether, followed by grinding, converted the crude gum to a pale orange powder which was dried under vacuum to provide the acid (3.35 g., 85%), M.P. from ca. 80° C. (decomp.); $[\alpha]_D^{26} = +112.9°$ (1%, methanol.

Found: C, 45.97; H, 6.29; N, 6.75%; Calculated for $C_{15}H_{22}N_2O_4 \cdot HBr \cdot H_2O$: C, 45.81; H, 6.41; N, 7.12%.

EXAMPLE 10

A. L,L-N-(N-tert-butyloxycarbonylisoleucyl)-2-(4-hydroxyphenyl)glycine

A solution of the product from Example 9, Part A (7.9 g., 0.02 mole) in a mixture of 1,4-dioxan (240 ml.) and water (60 ml.) was treated with a solution of sodium hydroxide (4.0 g., 0.1 mole) in water (100 ml.) as described in Example 8, Part A. The resulting, partially sticky, residue was triturated with n-hexane to furnish the product (6.3 g., 83%) as a pale pink powder after drying under vacuum, M.P. from ca. 102° C. (decomp.); $[\alpha]_D^{28} = 81.9°$ (1%, methanol).

Found: C, 59.92; H, 7.60; N, 7.07%; Calculated for $C_{19}H_{28}N_2O_6$: C, 59.98; H, 7.42; N, 7.36%.

B. L,L-N-isoleucyl-2-(4-hydroxyphenyl)glycine hydrobromide

The product from Part A, above (5.07 g., 0.013 mole) was treated with a 45% solution of hydrogen bromide in glacial acetic acid (15 ml.) as described in Example 7, Part B. Several triturations of the crude gum with ether, followed by rapid drying under vacuum, grinding, and further drying afforded the product (4.45 g., 86.5%) as a creamish-mauve powder, M.P. from ca. 145° C. (decomp.); $[\alpha]_D^{27} + +113.5°$ (1%, methanol).

Found: C, 47.62; H, 6.79; N, 6.54%; Calculated for $C_{14}H_{20}N_2O_4 \cdot HBr \cdot 1/3 Et_2O$: C, 47.71; H, 6.36; N, 7.28%.

EXAMPLE 11

When the procedure of Example 9 is repeated but using the N-hydroxysuccinimide esters of the t-Boc-amino acids indicated below in place of L-N-t-butyloxycarbonyl isoleucine N-hydroxysuccinimide ester, the following methyl L-2-(4-hydroxyphenyl)glycine dipeptides are obtained in a like manner as the hydrobromide salts.

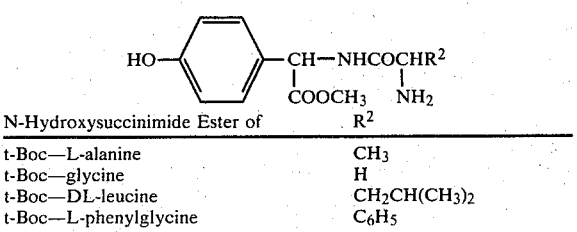

| N-Hydroxysuccinimide Ester of | $R^2$ |
|---|---|
| t-Boc—L-alanine | $CH_3$ |
| t-Boc—glycine | H |
| t-Boc—DL-leucine | $CH_2CH(CH_3)_2$ |
| t-Boc—L-phenylglycine | $C_6H_5$ |

| N-Hydroxysuccinimide Ester of | structure: HO-C6H4-CH(COOCH3)-NHCOCHR2-NH2, R2 |
|---|---|
| t-Boc—DL-phenylalanine | C6H5CH2 |
| t-Boc—L-tyrosine | 4-HOC6H5CH2 |
| t-Boc—L-valine | CH(CH3)2 |
| t-Boc—L-aspartic acid-β-methyl ester | CH2COOCH3 |
| t-Boc—L-glutamic acid-γ-ethyl ester | (CH2)2COOCH2CH3 |

The corresponding amino acids of formula II are obtained by the procedure of Example 10. The N-hydroxysuccinimide esters of the t-butyloxycarbonylamino acids were prepared by the method of Anderson, et al., J. Am. Chem. Soc., 86, 1839 (1964).

EXAMPLE 12

A. Isoelectric pH Precipitation of Dipeptides

The preparation of dipeptides of formula II ($R^1$=OH) is illustrated as follows:

L,L-N-[2-(4-Hydroxyphenyl)glycyl]-2-(4-hydroxyphenyl)glycine hydrobromide prepared as described in Example 3 (5 g.), is dissolved in a minimum amount of water. The solution was adjusted to the isoelectric pH (ca. 6) by means of dilute sodium hydroxide solution and allowed to stand overnight at 0°–5° C. The precipitated dipeptide was collected by filtration and dried.

B. Carboxylate Salt Formation

The dipeptide from Part A, above, is reslurried in a small amount of water and one equivalent of dilute sodium hydroxide solution is added. The resulting solution is stirred for 5–10 minutes then evaporated to dryness in vacuo to obtain the desired sodium salt.

When the above procedure is repeated but employing other bases in place of sodium hydroxide, such as, for example, potassium carbonate, ammonium hydroxide, calcium hydroxide and magnesium hydroxide, the corresponding potassium, ammonium, calcium and magnesium salts are similarly obtained.

C. Acid Addition Salts

The dipeptide from Part A, above, is reslurried in a small amount of water and an equivalent amount of acid such as hydrochloric, sulfuric, phosphoric, acetic, maleic, fumaric, lactic, tartaric, citric, gluconic, saccharic or p-toluenesulfonic acid is added. The resulting mixture is stirred for about 15 minutes then evaporated to dryness or precipitated by addition of a cosolvent such as methanol or ethanol.

EXAMPLE 13

Parenteral Solutions

A. Glacial acetic acid (12.0 gm.) and sodium acetate anhydrous (16.4 gm.) are each dissolved in 1000 ml. of freshly distilled water to produce 0.2 molar solutions. 148.0 ml. of the acetic acid solution is then mixed with 352.0 ml. of the sodium acetate solution and the mixture made up to 1000 ml. with freshly distilled water. L,L-N-[2-(4-hydroxyphenyl)glycyl]-2-(4-hydroxyphenyl)glycine, 10 g., is then added and the resulting 1% w/v solution is then sterilized by filtration through a suitable bacteria-proof filter under aseptic conditions into sterile 50 ml. glass vials, which when filled with 30 ml. of the final solution, contain 300 mg. of the active ingredient.

B. Succinic acid (23.62 gm.) and sodium hydroxide 98 g.) are each dissolved in 1000 ml. of freshly distilled water to produce 0.2 molar solutions. 250 ml. of the succinic acid solution is then mixed with 267.0 ml. of the sodium hydroxide and the mixture made up to 1000 ml. with freshly distilled water. L,L-methyl N-[2-(4-hydroxyphenyl)glycyl]-2-(4-hydroxyphenyl)glycinate, is then added and the resulting 1% w/v solution is then sterilized as in Part A, above. Sterile 50 ml. glass vials, when filled with 40 ml. of the final solution, contain 400 mg. of the active ingredient.

EXAMPLE 14

The following are typical tablet or capsule formulations containing L,L-2-isoleucyl-2-(4-hydroxyphenyl)glycine hydrobromide as active ingredient:

| | mg./tablet or capsule | | | | |
|---|---|---|---|---|---|
| | A | B | C | D | E |
| active ingredient | 500 | 100 | 100 | 25 | 25 |
| lactose | 30 | 170 | — | 220 | — |
| corn starch | 60 | 80 | — | 105 | — |
| microcrystalline cellulose ("Avicel") | — | — | 170 | — | 220 |
| glycine | — | — | 80 | — | 105 |
| Fine silica ("Aerosil") | — | 0.35 | 0.35 | 0.35 | 0.35 |
| Magnesium stearate* | 5 | 3 | 3 | 3 | 3 |
| | 595 | | | 353.35 | |

*9:1 blend with sodium lauryl sulphate "Avicel" and "Aerosil" are Trademarks.

For formulations A, B, and D, the ingredients are thoroughly blended together, and then either filled directly into hard gelatin capsules of appropriate size, or granulated and compressed into tablets of the desired size. For formulations C and E, the ingredients are thoroughly blended together and slugged. The slugs are broken down into granules, and then either filled into capsules of the appropriate size, or directly compressed into tablets of the desired size.

In formulations A, B and D, the lactose may be replaced by equal amounts of calcium carbonate or dicalcium phosphate.

EXAMPLE 15

Example 14 is repeated using the same amount of racemic DL,DL-isoleucyl-2-(4-hydroxyphenyl)glycine hydrobromide as that of the L,L-isomer. Of course, twice as many capsules or tablets of this example may be required to be taken for a single therapeutic administration as are required of the tablets or capsules of Example 14.

What is claimed is:

1. A method of treating a mammalian subject suffering from ischemic heart disease or cardiac failure attributable to reduced oxygen availability to the heart which comprises orally or parenterally administering to said subject from 25–1400 mg. per day of an L-derivative of p-hydroxyphenylglycine or 50–2800 mg. per day of a DL-derivative of p-hydroxyphenylglycine, said derivate having the formula

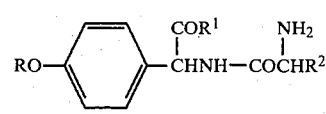

or a pharmaceutically acceptable salt thereof, wherein R is hydrogen or methyl;
$R^1$ is hydroxy, amino or alkoxy having from one to six carbon atoms;

R² is a member selected from the group consisting of hydrogen, phenyl, hydroxyphenyl, benzyl, p-hydroxybenzyl, alkyl having from one to six carbon atoms and —$(CH_2)_n COOR^5$, where n is 1 or 2 and $R^5$ is hydrogen, methyl or ethyl.

2. The method of claim 1 wherein said derivative is L,L-N-alanyl-2-(4-hydroxyphenyl)-glycine.

3. The method of claim 1 wherein said derivative is L,L-methyl-N-alanyl-2-(4-hydroxyphenyl)glycinate.

4. The method of claim 1 wherein said derivative is L,L-N-isoleucyl-2-(4-hydroxyphenyl)glycine.

5. The method of claim 1 wherein said derivative is L,L-methyl-N-isoleucyl-2-(4-hydroxyphenyl)glycinate.

6. The method of claim 1 wherein said derivative is L,L-N-[2-(4-hydroxyphenyl)-glycyl]-2-(4-hydroxyphenyl)glycine.

7. The method of claim 1 wherein said derivative is L,L-methyl-N-[2-(4-hydroxyphenyl)-glycyl]-2-(4-hydroxphenyl)glycinate.

8. A method according to claim 1 wherein the phenylglycine fragment has the L-configuration.

9. A method according to claim 1 wherein the aminoacyl fragment is present in the L-configuration.

10. The method according to claim 1 wherein R is hydrogen and $R^1$ is hydroxy or methoxy.

11. The method according to claim 10 wherein $R^2$ is 4-hydroxyphenyl.

12. The method according to claim 10 wherein $R^2$ is methyl.

13. The method according to claim 10 wherein $R^2$ is sec-butyl.

* * * * *